(12) United States Patent
Belzer

(10) Patent No.: US 8,770,460 B2
(45) Date of Patent: Jul. 8, 2014

(54) SHIELD FOR SURGICAL STAPLER AND METHOD OF USE

(76) Inventor: George E. Belzer, Minneapolis, MN (US)

( * ) Notice: Subject to any disclaimer, the term of this patent is extended or adjusted under 35 U.S.C. 154(b) by 327 days.

(21) Appl. No.: 12/644,236

(22) Filed: Dec. 22, 2009

(65) Prior Publication Data

US 2010/0163598 A1   Jul. 1, 2010

Related U.S. Application Data

(60) Provisional application No. 61/140,501, filed on Dec. 23, 2008, provisional application No. 61/142,695, filed on Jan. 6, 2009.

(51) Int. Cl.
*A61B 17/10* (2006.01)
*A61B 17/04* (2006.01)

(52) U.S. Cl.
USPC .................................................. 227/179.1

(58) Field of Classification Search
USPC ...................... 227/175.1–182.1, 19
See application file for complete search history.

(56) References Cited

U.S. PATENT DOCUMENTS

| | | | |
|---|---|---|---|
| 1,937,294 A * | 11/1933 | Post ............................. | 392/384 |
| 2,466,042 A * | 4/1949 | Reich et al. .................. | 607/105 |
| 3,193,185 A | 7/1965 | Gueorguievich et al. | |
| 4,182,474 A * | 1/1980 | Sato ............................. | 227/99 |
| 4,195,624 A | 4/1980 | Douglas | |
| 4,473,077 A | 9/1984 | Noiles et al. | |
| 4,488,523 A | 12/1984 | Shichman | |
| 4,505,414 A * | 3/1985 | Filipi ............................ | 227/19 |
| 4,576,167 A | 3/1986 | Noiles | |
| 4,646,745 A | 3/1987 | Noiles | |
| 4,754,909 A | 7/1988 | Barker et al. | |
| 4,848,367 A * | 7/1989 | Avant et al. .................. | 128/898 |
| 4,873,977 A * | 10/1989 | Avant et al. ................. | 227/180.1 |
| 5,047,039 A * | 9/1991 | Avant et al. .................. | 606/148 |
| 5,104,025 A | 4/1992 | Main et al. | |
| 5,205,459 A | 4/1993 | Brinkerhoff et al. | |

(Continued)

FOREIGN PATENT DOCUMENTS

WO   WO 02/00121   1/2002

OTHER PUBLICATIONS http://dictionary.reference.com/browse/INTEGRAL—Dictionary Definition of Integral.*

(Continued)

*Primary Examiner* — Robert Long
(74) *Attorney, Agent, or Firm* — Dorsey & Whitney LLP

(57) ABSTRACT

A surgical stapler that may have a head assembly, a stapling assembly, a shield, a base head, a handle assembly, and a shaft assembly. A head assembly may have an anvil and anvil shaft, as well as a stapling assembly. A stapling assembly may have a trocar that can be removeably detachable with the anvil, a cannula extension, and a plurality of staples. A shield may be configured to retract from a first extended position where the shield generally covers the stapling assembly or the head assembly, to a second retracted position where the shield generally exposes the stapling assembly or the head assembly. The shield may be integral with the stapler, or provided after-market as an add-on. A surgical stapler may additionally or alternatively include an air or gas pump assembly that can be used to insufflate the rectum and intestinal tract during insertion and advancement of the stapler.

8 Claims, 14 Drawing Sheets

(56) References Cited

U.S. PATENT DOCUMENTS

| | | | |
|---|---|---|---|
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| D357,535 S | 4/1995 | Grant et al. | |
| 5,404,870 A | 4/1995 | Brinkerhoff et al. | |
| 5,445,644 A | 8/1995 | Pietrafitta et al. | |
| 5,571,153 A * | 11/1996 | Wallsten | 607/98 |
| 5,588,579 A | 12/1996 | Schnut et al. | |
| 5,669,918 A * | 9/1997 | Balazs et al. | 606/139 |
| 5,836,503 A | 11/1998 | Ehrenfels et al. | |
| 6,066,132 A * | 5/2000 | Chen et al. | 606/28 |
| 6,119,913 A | 9/2000 | Adams et al. | |
| 6,174,318 B1 * | 1/2001 | Bates et al. | 606/127 |
| 6,244,491 B1 * | 6/2001 | Kandasamy et al. | 227/134 |
| 6,338,737 B1 * | 1/2002 | Toledano | 606/219 |
| 6,957,758 B2 | 10/2005 | Aranyi | |
| 6,994,667 B2 * | 2/2006 | Singh | 600/105 |
| 7,021,512 B1 * | 4/2006 | Nakamura | 227/76 |
| 7,182,239 B1 | 2/2007 | Myers | |
| 7,401,722 B2 | 7/2008 | Hur | |
| 7,451,765 B2 * | 11/2008 | Adler | 128/207.14 |
| 7,547,312 B2 * | 6/2009 | Bauman et al. | 606/151 |
| 7,845,536 B2 * | 12/2010 | Viola et al. | 227/179.1 |
| 7,951,071 B2 * | 5/2011 | Whitman et al. | 600/121 |
| 2001/0041899 A1 * | 11/2001 | Foster | 606/127 |
| 2003/0014064 A1 * | 1/2003 | Blatter | 606/153 |
| 2003/0028178 A1 | 2/2003 | Chin | |
| 2003/0029451 A1 * | 2/2003 | Blair et al. | 128/204.18 |
| 2005/0051597 A1 * | 3/2005 | Toledano | 227/176.1 |
| 2005/0066969 A1 * | 3/2005 | Rick et al. | 128/204.18 |
| 2005/0145675 A1 * | 7/2005 | Hartwick et al. | 227/180.1 |
| 2005/0187576 A1 * | 8/2005 | Whitman et al. | 606/219 |
| 2005/0274768 A1 * | 12/2005 | Cummins et al. | 227/175.1 |
| 2006/0201989 A1 * | 9/2006 | Ojeda | 227/175.1 |
| 2006/0271094 A1 * | 11/2006 | Hudson et al. | 606/196 |
| 2007/0060952 A1 | 3/2007 | Roby et al. | |
| 2007/0118157 A1 | 5/2007 | Zuidema et al. | |
| 2008/0243176 A1 * | 10/2008 | Weitzner et al. | 606/206 |
| 2009/0114233 A1 * | 5/2009 | Edoga et al. | 128/898 |
| 2009/0204108 A1 | 8/2009 | Steffen | |
| 2009/0264914 A1 * | 10/2009 | Riina et al. | 606/191 |
| 2010/0288815 A1 * | 11/2010 | Maemori | 227/127 |
| 2011/0042442 A1 * | 2/2011 | Viola et al. | 227/179.1 |
| 2011/0114699 A1 * | 5/2011 | Baxter et al. | 227/175.1 |
| 2011/0118761 A1 * | 5/2011 | Baxter et al. | 606/148 |
| 2011/0163147 A1 * | 7/2011 | Laurent et al. | 227/175.2 |
| 2011/0248067 A1 * | 10/2011 | Takei | 227/175.1 |

OTHER PUBLICATIONS http://dictionary.reference.com/browse/INTEGRAL—Dictionary Definition of Integral—Jul. 5, 2011.*

Guweidhi, Ahmed et al., "Circular Stapler Introducer: A Novel Device to Facilitate Stapled Colorectal Anastomosis", Diseases of the Colon & Rectum vol. 52: 4, pp. 746-748, 2009.

* cited by examiner

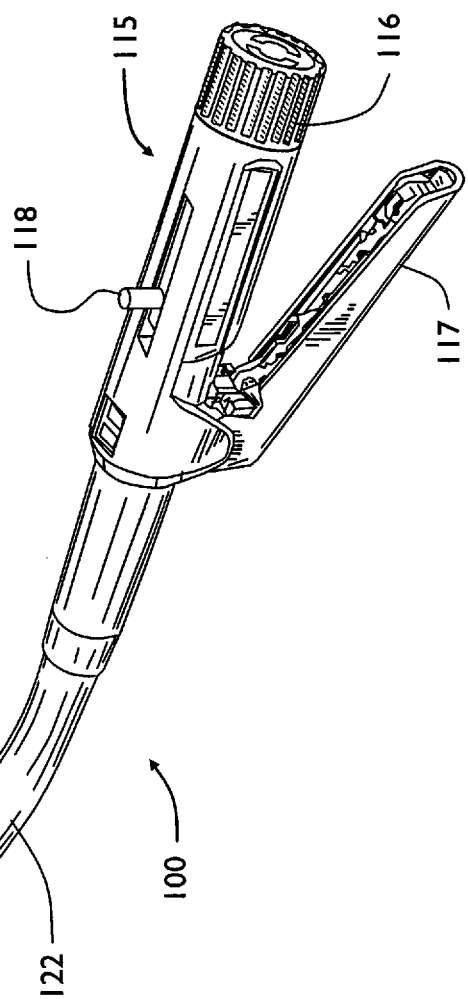
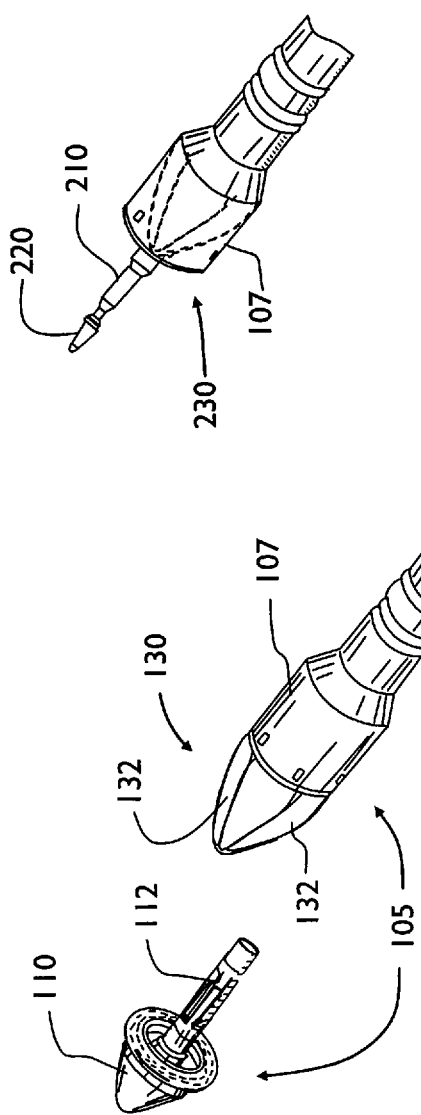
FIG. 2a
FIG. 1

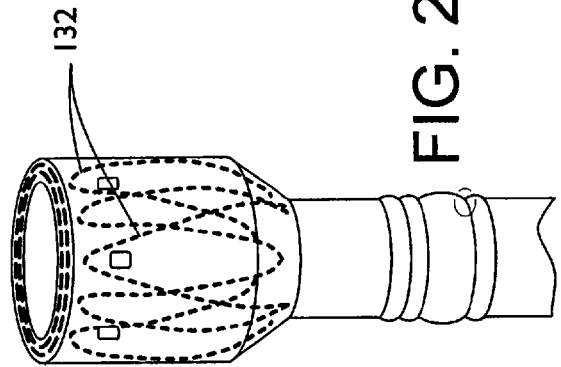
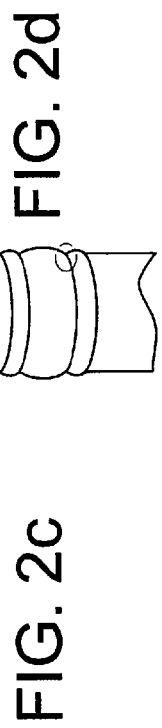
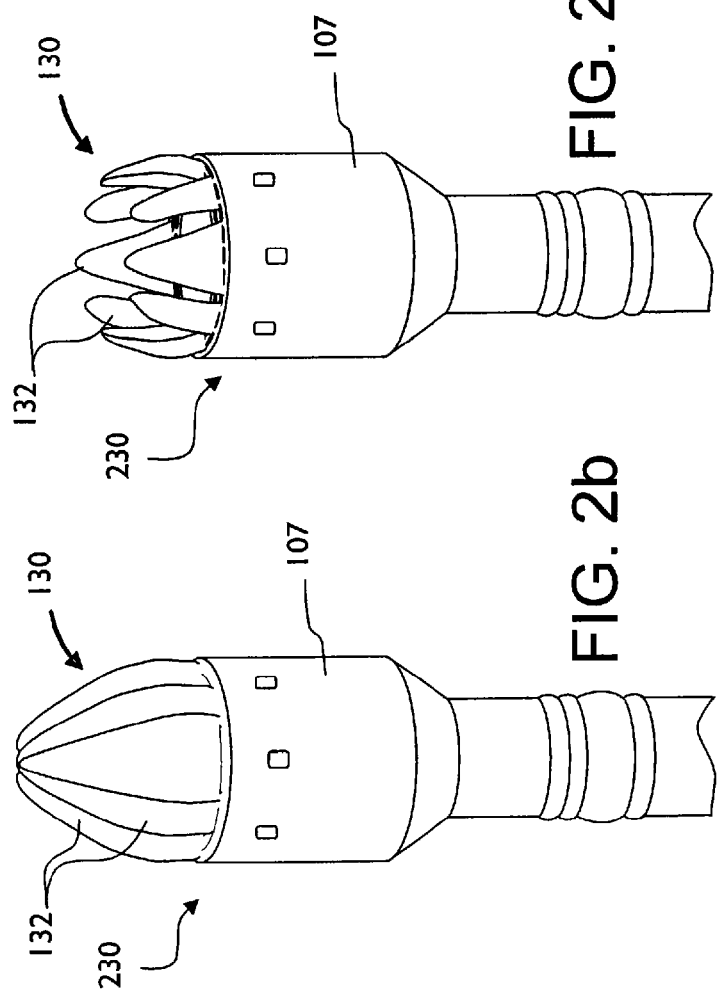
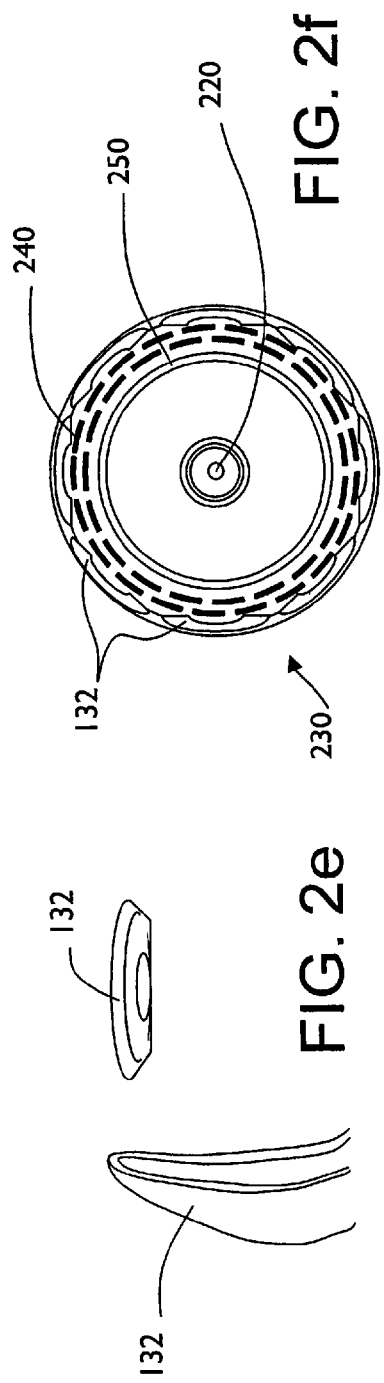

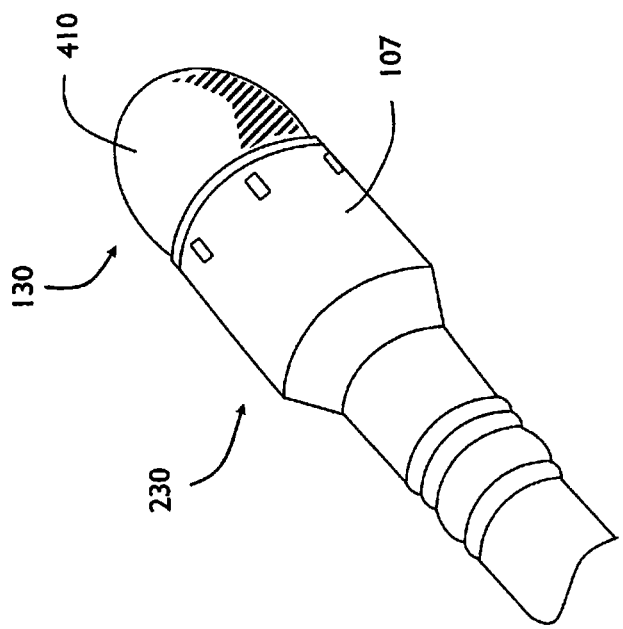
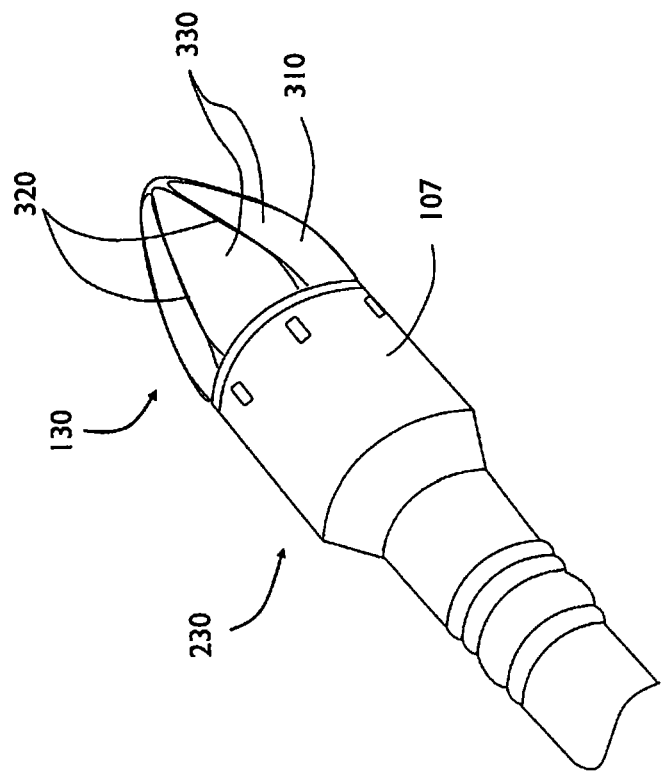
FIG. 4
FIG. 3

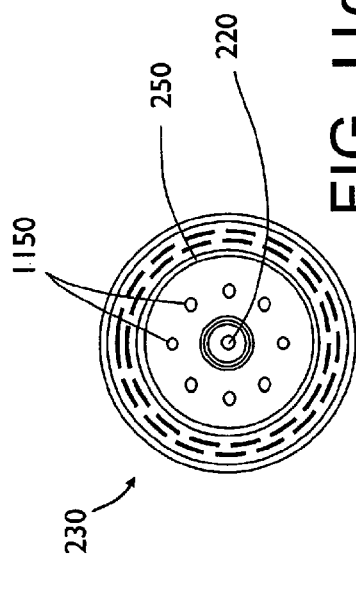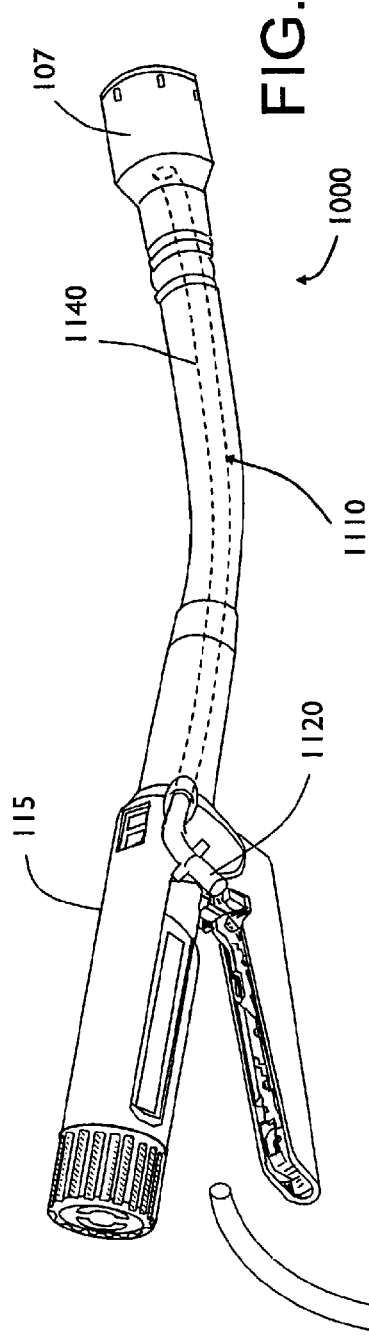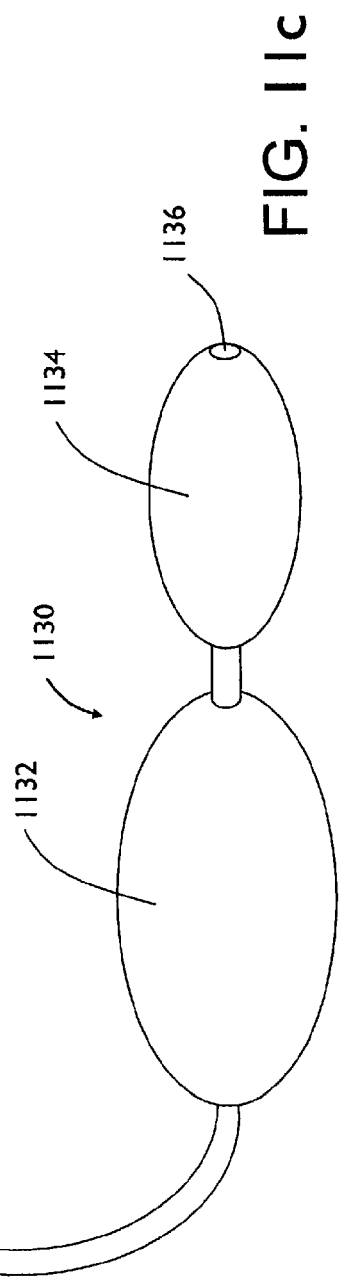

SHIELD FOR SURGICAL STAPLER AND METHOD OF USE

CROSS-REFERENCE TO RELATED APPLICATIONS

This application claims benefit of priority to U.S. Provisional Application No. 61/140,501 filed Dec. 23, 2008 and U.S. Provisional Application No. 61/142,695 filed Jan. 6, 2009, the contents of each are herein incorporated by reference.

FIELD OF THE INVENTION

The present disclosure relates to an apparatus and method for guiding a surgical stapler through a length of intestinal tract in a streamlined and/or navigable manner. More particularly the present disclosure relates to a retractable cover or shield to facilitate passage of a surgical stapler through the intestinal tract, allowing the surgeon to minimize or avoid trauma to the intestinal tract during insertion of the stapler, and to negotiate and dilate intestinal strictures and naturally occurring intestinal valves and curves.

BACKGROUND OF THE INVENTION

The use of surgical staples to construct intestinal anastomosis is known. In an anastomotic stapling surgery, usually two pieces of tubular tissue are attached together by a ring of staples. Various anastomotic techniques are known including attaching the two pieces of tubular tissue end to end, end to side, and side to side. During construction of stapled end to end, or end to side anastomosis, a circular stapling device is often used. Circular stapling devices are most often used for colon and rectal surgery, whereby a diseased portion of the bowel is removed and the proximal and distal intestinal segments are joined together by means of a circular stapler to reestablish intestinal continuity. A circular stapling device may generally include a head assembly, a stapling assembly, a shaft assembly, a handle assembly, and a head base. In performing an anastomosis with such a stapling instrument, the two pieces of tubular tissue are clamped together between an anvil that has a circular array of staple-forming grooves and a staple holder that has a plurality of staple-receiving slots arranged in a circular array in which the staples are received. A staple pusher is advanced to drive the staples into the tissue and form the staples against the anvil. Present circular anastomosis stapling instruments include, for example, U.S. Pat. No. 5,205,459 to Brinkerhoff et. al. and U.S. Pat. Nos. 4,576,167 and 4,646,745 to Noiles, each of which is hereby incorporated herein by reference in its entirety.

Sometimes, a circular anastomosis stapling instrument may be provided with a flexible shaft that allows the head assembly to assume various positions relative to the actuator assembly. For example U.S. Pat. No. 4,473,077 to Noiles et. al., U.S. Pat. No. 4,754,909 to Barker et. al., and U.S. Pat. No. 4,488,523 to Shichman, each of which is hereby incorporated by reference herein in its entirety, disclose circular stapling instruments with flexible shafts.

One method of constructing an anastomosis includes a double purse string suture technique. In preparation for the anastomosis, purse string sutures are placed in both the proximal and distal ends of the lumen to be connected. Typically, the anvil is secured in the proximal bowel, and the circular stapler with the anvil detached is inserted into the anal opening of the patient and up through the appropriate length of rectum. During passage of a circular stapler without the anvil portion attached, the attendant bowel may be traumatized and or irritated by blunt, sharp, cornered, etc. surfaces of the stapling assembly. At other times, the circular stapler with the anvil detached may not be able to negotiate the bowel with relative ease because of strictures in the walls of the bowel and naturally occurring intestinal valves and curves.

In another version of the double purse string suture technique, a circular stapler, with the anvil attached, is passed through the anus to the distal end of the lumen, which has been secured by a purse string suture. The purse string suture must then be opened wide enough to allow the entire anvil to be extended through the distal end of the lumen and into the proximal end of the lumen. The distal purse string suture is then pulled tight, gathering the tissue about the extended trocar, and the proximal purse string suture is pulled tight, gathering the tissue about the anvil shaft. The actuator is then engaged, which brings the anvil and the stapling assembly together, resulting in a ring of staples about the perimeter of the now connected lumen. When the circular stapler is passed through the intestinal tract as one unit, as in this technique, the need to open the distal purse string suture wide enough to allow the anvil to pass through the end of the distal lumen may result in intestinal content spillage, which may lead to increased rates of postoperative infection. Even with the anvil attached to the stapler, the shape of the anvil may not be streamlined, and trauma to the intestine may occur when the stapler is passed through the intestinal tract.

Another technique of constructing an anastomosis includes using a purse string suture at the proximal end of the lumen and staples at the distal end of the lumen. This type of anastomosis is often referred to as a double staple technique. This method can be advantageous because it does not require the placement of a purse string suture about the end of the distal lumen, which can be difficult to apply and, as stated above, may result in intestinal content spillage. Otherwise, this technique is performed in generally the same manner as the first method described above for the double purse string technique, whereby the stapler with the anvil detached is inserted through the anus to the distal end of the lumen, and the anvil is inserted in the proximal end of the lumen. The same limitations as the earlier described technique are attendant in this technique, namely that the passage of the circular stapler without the anvil, may cause bowel irritation and or trauma. Further, the stapler, without the anvil may be difficult to negotiate through the intestinal tract due to strictures, and or naturally occurring curves, twists, and valves.

As more colon and rectal procedures are performed laparoscopically, a need in the art exists for a circular stapler that can be more easily passed through the bowel when the anvil is not attached. There exists a need in the art for a retractable cover or shield to facilitate passage of a surgical stapler through the intestinal tract, allowing the surgeon to minimize or avoid trauma to the intestinal tract during insertion of the stapler, and to negotiate and dilate intestinal strictures. There also exists a need in the art for a surgical stapler including an air or gas pump assembly that can be used to insufflate the rectum and intestinal tract during insertion and advancement of the stapler.

BRIEF SUMMARY OF THE INVENTION

The present disclosure relates to a surgical stapler device with a retractable atraumatic cover or shield to allow easier passage of a stapler through the anus/rectum/colon. A retractable shield can be connected to a head base, whereby when in an extended position, the shield may generally cover a head assembly or a stapling assembly forming a streamlined tip. A cover or shield can be controlled by cables, wires, or other suitable means, that extend from a handle of the device to the head assembly. The shield can be retracted when the stapler is appropriately positioned by deploying an actuator or trigger on the stapler handle assembly. A retractable shield can help guide the stapling device with or without an anvil attached, which may reduce trauma or irritation to the bowel associated with passage of a stapler through the intestinal tract of a patient. A retractable shield can also improve the ability to position the stapler, permitting navigation about strictures in the intestine, and naturally occurring curves, twists and valves, which can also reduce trauma to the intestine. The anal canal may also be less likely to be traumatized during insertion of a streamlined shield. A reduction in trauma and easier advancement of a stapler may reduce both surgical times and technical difficulties. In some embodiments, a retractable atraumatic cover or shield may be formed by a plurality of petal-shaped segments, a peel-away sheath, an inflatable balloon, or any other suitable design which can be withdrawn into the head base. In an alternative embodiment, the shield may be retracted alongside the outer circumference of the head base. In yet a further embodiment, the shield may be removably attachable, and may be provided after-market from the surgical stapler itself, such that the shield may be attached to the surgical stapler any time prior to insertion of the stapler through the anus/rectum/colon. The shield could be made of any suitable material such as, but not limited to plastic or metal.

The present disclosure, in one embodiment, relates to a surgical stapler that may have a head assembly, a stapling assembly, a handle assembly, a shaft assembly, a head base and a shield. A head assembly may have an anvil, including an anvil shaft, and a stapling assembly. A stapling assembly may have a trocar, a cannula extension, a cutting knife/blade, and a plurality of staples. A shield may be configured to retract from a first extended position where the shield generally covers the head assembly or the stapling assembly, to a second retracted position where the shield generally exposes the head assembly or the stapling assembly. The anvil may have an anvil shaft that may be attached to, or removed from the trocar. The handle assembly may have an actuator for controlling the shield. The shaft assembly may connect the head assembly and the handle assembly.

The present disclosure, in another embodiment, relates to a surgical stapler that may include an air pump assembly that can be used to insufflate the intestinal walls, thereby reducing trauma to the intestine during passage of a surgical stapler. The air pump assembly may include an inner tubing, a connector, an outer tubing, and an air outlet. The air pump assembly can be used to force air from the outer tubing, to the inner tubing and through the air outlet into the intestinal cavity. As air is forced into the intestine, the intestinal wall may dilate, making passage and navigation of the surgical stapler easier, thereby reducing the amount of trauma caused by the stapler. The air pump assembly could be used with staplers that include shields, as well as staplers that do not include shields. The air pump assembly could also be used with or without the anvil attached to the stapling assembly.

The present disclosure, in another embodiment, relates to a method for constructing an anastomosis with a surgical stapler. The surgical stapler may include a head assembly that may have an anvil, including an anvil shaft, and a stapling assembly. A stapling assembly may include a trocar, a cannula extension, a cutting knife/blade, and a plurality of staples. A shield may be configured to retract from a first extended position, where the shield generally covers the head assembly or the stapling assembly, to a second retracted position, where the shield generally exposes the head assembly or the stapling assembly. The anvil may also have an anvil shaft that may be attached to, or removed from the trocar. The surgical stapler may also have a handle assembly with an actuator for controlling the shield when the shield is in the first extended position. The method may be performed by securing an end of a first lumen, and inserting the surgical stapler into and through the first lumen to the secured end. The shield may be retracted from the first position to the second position, allowing the trocar to be passed through the secured end of the first lumen. The anvil, including an anvil shaft, may be inserted into a second lumen with the anvil shaft exposed. After the trocar and the anvil shaft are connected, a second actuator on the handle assembly of the stapler may be engaged to drive the anvil and stapling assembly together, thereby stapling the first and second lumens together. Finally, the surgical stapler may be removed from the patient.

The present disclosure, in a further embodiment, relates to an anastomosis surgical stapler that may have a shield that can be configured to extend to a first position, wherein the shield at least partially covers a head assembly, or a stapling assembly, and retracts to a second position, wherein the shield at least partially exposes the head assembly or the stapling assembly.

The present disclosure, in yet a further embodiment, relates to a surgical stapler including an air or gas pump assembly that can be used to insufflate the rectum and intestinal tract during insertion and advancement of the stapler. The stapler may or may not include a retractable shield.

While multiple embodiments are disclosed, still other embodiments of the present disclosure will become apparent to those skilled in the art from the following detailed description, which shows and describes illustrative embodiments of the invention. As will be realized, the embodiments described herein are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the disclosure will be better understood from the following description taken in conjunction with the accompanying Figures, in which:

FIG. 1 is a perspective view of a surgical stapler with a retractable shield or cover shown in an extended position in accordance with one embodiment of the present disclosure.

FIGS. 2 a-f are various views of a retractable shield in different states of retraction into or extension from the head base of a surgical stapler in accordance with one embodiment of the present disclosure.

FIG. 3 is a perspective broken view of a stapling assembly of a surgical stapler, wherein a retractable peel-away sheath is shown in a first extended position in accordance with another embodiment of the present disclosure.

FIG. 4 is a perspective broken view of a stapling assembly of a surgical stapler, wherein an inflatable balloon is shown in the inflated position in accordance with a further embodiment of the present disclosure.

FIGS. 11 a-d are various views of a surgical stapler with an air or gas pump assembly in accordance with an embodiment of the present disclosure.

DETAILED DESCRIPTION

Figure 5:
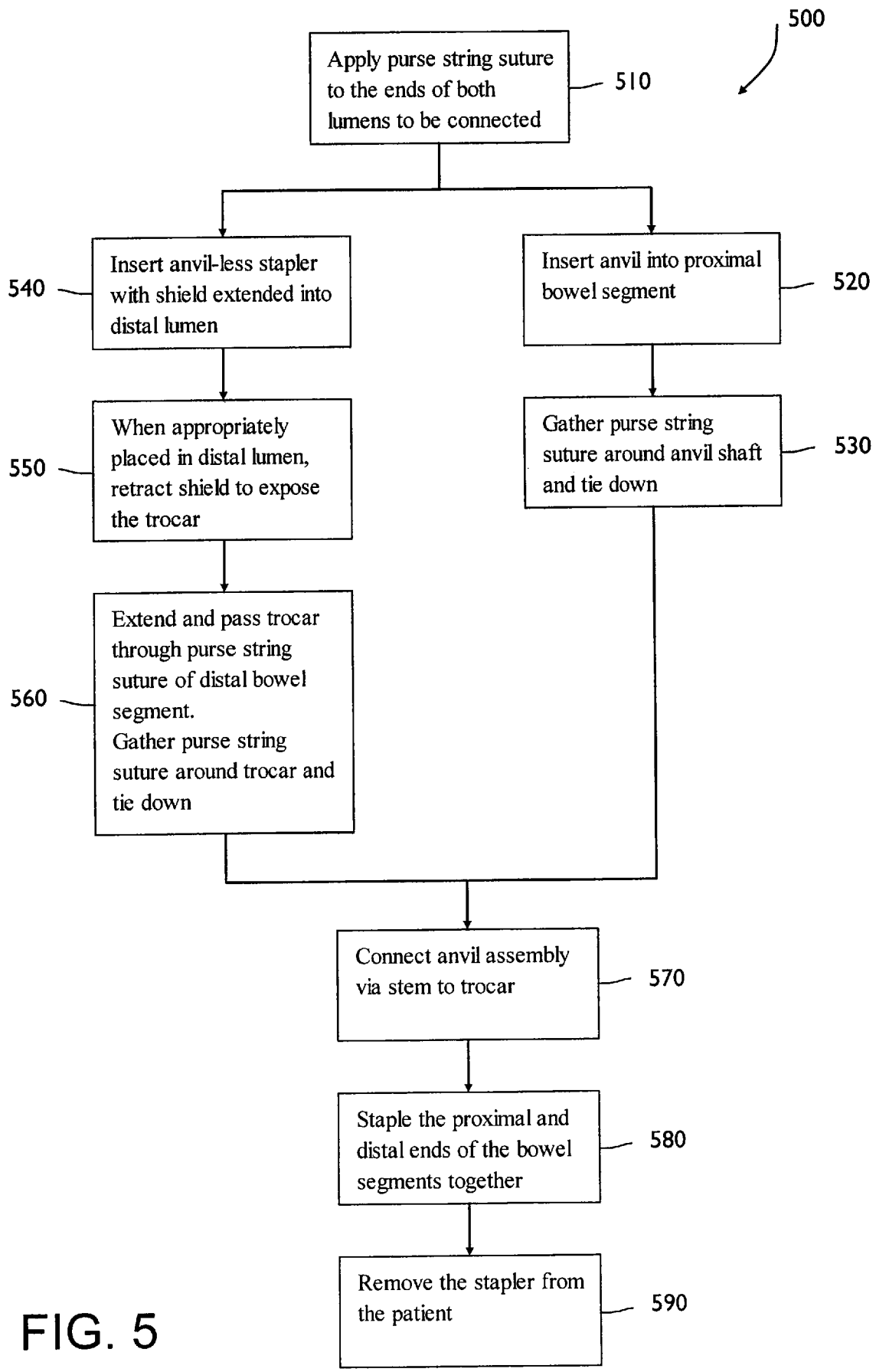
FIG. 5 is a flow diagram of a method for constructing an anastomosis with a surgical stapler with a retractable shield or cover, according to one embodiment of the present disclosure, by using double purse string sutures to secure the ends of the lumens to be connected.

The present disclosure relates to novel and advantageous retractable covers or shields for a surgical stapler and a method for their use. A surgical stapler shield may allow for easier passage of a surgical stapler when an anvil is removed. When the shield is appropriately extended over the head assembly or the stapling assembly, the surgical stapler can become more streamlined or navigable, which may allow for easier navigation of an intestinal tract. Consequently, intestinal irritation and trauma may be reduced. A cover or shield may also make it easier to navigate through and around strictures, valves, and naturally occurring curves in an intestinal wall. In one embodiment, the shield may be removably attachable, and may be provided after-market from the surgical stapler itself, such that the shield may be attached to the surgical stapler any time prior to insertion of the stapler through the anus/rectum/colon. The present disclosure also relates to a surgical stapler including an air or gas pump assembly that can be used to insufflate the rectum and intestinal tract during insertion and advancement of the stapler.

In an anastomotic stapling surgery, usually two pieces of tubular tissue are attached together by a ring of staples. Various anastomotic techniques could be used, including attaching the two pieces of tubular tissue end to end, end to side, and side to side. During construction of stapled end to end, or end to side anastomosis, a stapling device can be used. Stapling devices are most often used for colon and rectal surgery, whereby a diseased portion of the bowel is removed and the proximal and distal intestinal segments may be joined together by means of a stapler to reestablish intestinal continuity. In one embodiment, a stapling device may include a head assembly, a stapling assembly, a shaft assembly, a handle assembly, a shield, and a head base. In performing an anastomosis with such a stapling instrument, the two pieces of tubular tissue may be clamped together between an anvil that may include a circular array of staple-forming grooves and a staple holder that may include a plurality of corresponding staple-receiving slots in which the staples are received. A staple pusher may be advanced to drive the staples into the tissue and form the staples against the anvil, thereby establishing anastomosis of the two pieces of tissue.

While generally described herein with respect to constructing an anastomosis, it will be understood by those skilled in the art that a surgical stapler device according to the various embodiments of the present disclosure may be used for other surgical applications, such as other surgical operations involving a lumen where a surgical stapler may be advantageous, and easier passage of the stapler may be desirable, such as but not limited to an esophageal tract.

FIGS. 1 and 2a-f show one embodiment of an anastomosis surgical stapler 100, according to the present disclosure. The stapler 100 may include a head assembly 105, a stapling assembly 230, an actuator handle assembly 115, a shield 130, a head base 107, and a shaft assembly 120 extending between the head assembly 105 and handle assembly 115. As seen in FIGS. 1 and 2a-f, the head assembly 105 may include an anvil 110, including anvil shaft 112, and a stapling assembly 230. The stapling assembly 230, in one embodiment, may include a cannula extension 210, a trocar 220, a circular cutting knife/blade 250, a plurality of staples 240, or any other suitable tools for carrying out anastomosis. Extension 210 may be extended out from, or retracted into, head base 107. Anvil 110 can be detachably secured to extension 210, via anvil shaft 112, for movement therewith to, for example, staple tissue positioned between anvil 110 and head base 107 together, as will be understood by those skilled in the art.

Handle assembly 115 may provide an area for gripping and controlling stapler 100. Handle assembly 115 may include any necessary, desirable, or useful controls for operating the stapler 100, and particularly for operating head assembly 105 during a surgical procedure. In one embodiment, handle assembly may include an actuator, control knob, dial, trigger, or any other suitable means 116 for controlling the motion of extension 210, such as, the extension and retraction of extension 210 from head base 107. As illustrated in FIG. 1, in one embodiment, actuator 116 could be an adjustment knob rotatably mounted on an end of actuator handle assembly 115. Handle assembly 115 may include another actuator, control knob, dial, trigger, or any other suitable means 117 to actuate the stapling motion, or perform the stapling act, whereby the anvil 110 is pulled in contact with or driven against head base 107 to staple tissue positioned between anvil 110 and head base 107 together, as will be understood by those skilled in the art.

Support shaft 122 may be any suitable length and may be made of any suitable material or surgical material, as will be understood by those skilled in the art. In one embodiment, support shaft 122 can be made of a flexible or tubular material to allow surgical stapler 100 to conform to twists or turns in an intestinal tract. Support shaft 122 may house all necessary connections, cables, wires, etc. for connecting the controls of handle assembly 115 with the corresponding controlled part or parts of head assembly 105. Support shaft 122 may be made of any suitable material, such as plastic, metal or metal alloy, any other suitable surgical or biocompatible material, or any combination thereof. In some embodiments, support shaft 122 may be flexible and/or made of a flexible material, so as to allow the head assembly 105 to assume various positions relative to the handle assembly 115.

In a further embodiment in accordance with the present disclosure, stapler 100, and in particular embodiments, head base 107 may be provided with a retractable shield, cover, sheath, etc. 130, which may allow the head assembly 105, or the stapling assembly 230 (i.e., the head assembly without the anvil attached to the stapler) to become more streamlined or navigable, and may further allow for easier navigation of the head assembly 105 or the stapling assembly 230 through the intestinal tract of a patient. Consequently, intestinal irritation and trauma may be reduced with the use of a surgical stapler cover or shield, as described herein. Shield 130 may also make it easier to navigate through and around strictures in an intestinal wall.

FIGS. 2a-f show various views of a retractable shield in different states of retraction into or extension from the head base of a surgical stapler in accordance with one embodiment of the present disclosure. FIG. 2a shows a perspective view of stapling assembly 230 with a shield 130 fully retracted into head base 107 and extension 210 extended from head base 107. FIG. 2b shows shield 130 in an extended position. FIG. 2c shows a plurality of segments 132 of shield 130 being partially extended from or retracted into head base 107. FIG. 2d shows shield 130 substantially fully retracted into head base 107. A side view and a top view of an individual segment 132 is shown in FIG. 2e in accordance with one embodiment of the present invention. FIG. 2f shows a top view of stapling assembly 230 with a shield 130 fully retracted into head base 107. In other embodiments, the shield 130 may be retracted alongside the exterior of head base 107. Trocar 220, staples 240, and cutting knife 250 can generally be exposed when shield 130 is fully retracted. As can best be seen in FIGS. 2a-2f, the shield 130 may be retracted from a first extended position as shown in FIG. 2b to a second retracted position as shown in FIG. 2d, vice versa, or adjusted to a position anywhere therebetween as shown in FIG. 2c, in accordance with one embodiment of the present disclosure. In an extended position, as illustrated in FIG. 1 and FIG. 2b, the shield 130 may generally cover the stapling assembly 230, thereby creating a generally streamlined shape that can be inserted into the anus/colon/rectum of a patient. In another embodiment shield 130 can cover head assembly 105, which includes the stapling assembly 230 and the anvil 110.

Figure 12A:
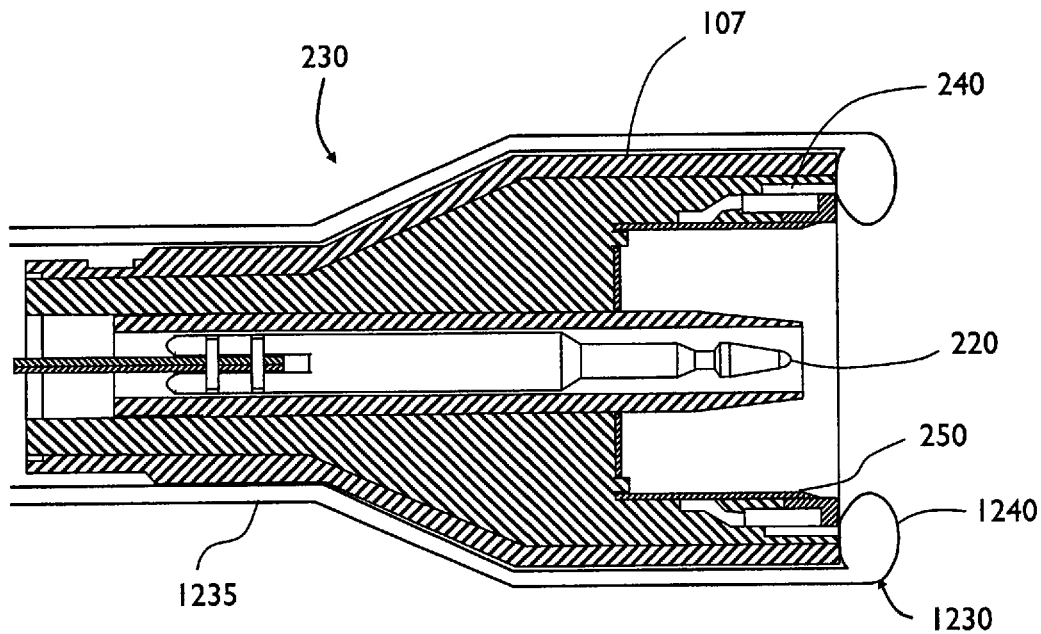
FIG. 12a is a cross-sectional view of a stapling assembly and shield according to one embodiment of the present disclosure, where the shield is configured to cover the edge(s) of the head base.
Figure 12B:
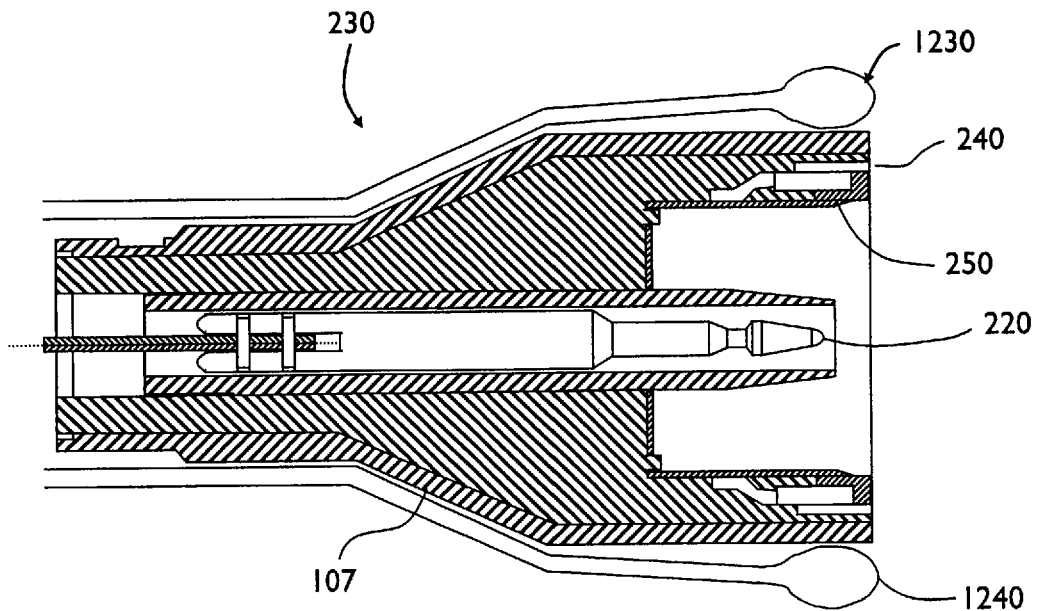
FIG. 12b is a cross-sectional view of the stapling assembly and shield of FIG. 12a, where the shield is retracted to a retracted position, exposing the staples.

In yet another embodiment, rather than generally covering the stapling assembly 230, thereby creating a generally streamlined shape that can be inserted into the anus/colon/rectum of a patient, the shield may be configured to simply cover the edge or edges of the generally circular head base 107, without necessarily covering the entire diameter of the head base 107. An example of such an embodiment is illustrated in FIGS. 12a and b, which show a stapling assembly 230 and shield 1230. In an extended position, as shown in FIG. 12a, the shield 1230 may generally cover the edge(s) of the generally circular head base 107 and the staples 240. In further embodiments, the shield 1230 may extend further across the diameter of the head base 107 to also cover or partially cover the cutting knife 250 and trocar 220. The shield 1230 may include a sleeve member 1235 and a shield tip 1240. The sleeve member 1235 may generally wrap around at least a portion of the head base 107, but need not entirely cover the head base. The shield tip 1240 may generally cover or partially cover the circumference of the head base 107, at its edge(s). As illustrated, the shield tip 1240 has a generally round configuration; however, it is recognized that any other suitable configuration may be used that may allow at least partial coverage of the edge(s) of the head base 107 and ease passage of the surgical stapler through the anus/colon/rectum of a patient. The shield 1230 may be retracted from the extended position, shown in FIG. 12a, to a retracted position, shown in FIG. 12b, or to any position therebetween. In the retracted position, the shield tip 1240 may be retracted to generally expose the staples 240.

Shield 130 may be controlled by cables, wires, or any other suitable means that can extend from the handle assembly 115 of stapler 100 to shield 130. Shield 130 can be appropriately retracted, for example when the stapler 100 is appropriately positioned in the anus/colon/rectum of a patient, by deploying an actuator 118 located on the actuator handle assembly 115.

The actuator, control knob, dial, trigger, or any other suitable means 118 may be provided on actuator handle assembly 115 and may be used, as generally stated above, to retract and/or extend shield 130 as appropriate. As seen in FIG. 1, in one embodiment of the present disclosure, actuator 118 may be a locking, slide engagement 118.

Shield 130 may comprise any suitable mechanism, including any suitable configuration, shape, and size, which allows shield 130 to be extended to a first position to generally partially or fully cover or enclose stapling assembly 230, or head assembly 105 and to be retracted to a second position into or alongside the outer circumference of head base 107, generally partially or fully exposing stapling assembly 230 or head assembly 105. In one embodiment, shield 130 may be fully retracted into or alongside head base 107, while in other embodiments, shield 130 may be partially retracted into head base 107. In one embodiment, as shown in FIGS. 1 and 2a-f, shield 130 may be made up of a plurality of shield members or petal-like members 132, which when extended, may be generally adjacent to one another, mate with one another, come in contact with one another, align with one another, etc., such that the petal-like members 132 generally partially or fully cover or enclose stapling assembly 230 or head assembly 105. In a retracted position, the petal-like members 132 of shield 130 may be retracted into head base 107 or alongside the outer circumference of head base 107 in a generally separated manner. When shield 130 is retracted into or alongside head base 107, trocar 220 can be generally exposed and may be extended.

In one embodiment of the present disclosure, a plurality of petal-like members 132 can include anywhere from 2 members to 10 members or more, and preferably may include from 2 members to 4 or 5 members. The petal-like members 132 can be made of any suitable material, including but not limited to, plastic, metal or metal alloy, any other suitable surgical or biocompatible material, or any combination thereof. Each petal-like member 132 may be generally petal-shaped, tear-drop-shaped, elliptical, oval, feather-shaped, palm leaf-shaped, or other suitable shape. In one embodiment, the petal-like members 132 may generally form a dome over the stapling assembly 230 or head assembly 105, culminating in a generally smooth or streamlined tip, wherein each of the tips of each of the members 132 are generally in contact with or adjacent to one another. In other embodiments, as described in detail above, the shield may simply cover the edge(s) of the stapling assembly 230, without necessarily covering the entire diameter of the head base 107.

In another embodiment, shown in FIG. 3, shield 130 can be a peel-away sheath 310. In one embodiment the peel-away sheath 310 might be a one-time use shield and may be discarded following the anastomosis. Engaging actuator 118 on actuator handle assembly 115 may, in such an embodiment, retract the peel-away sheath 310. In one embodiment, the peel-away sheath 310 may initially be provided in an extended position, generally partially or fully covering stapling assembly 230, or head assembly 105. The peel-away sheath 310 may include one or more peel lines, stress lines, tear lines, perforated lines, or otherwise weakened areas 320 at or along which a plurality of petal-like or other shaped members 330 may separate and be pulled away, or retracted, generally partially or fully exposing stapling assembly 230, or head assembly 105. Peel-away sheath 310 could be smooth and/or generally form a rounded tip or dome over stapling assembly 230, or head assembly, which can make it easier to insert the stapler into the intestinal tract of a patient. In other embodiments, as described in detail above, the shield may simply cover the edge(s) of the stapling assembly 230, without necessarily covering the entire diameter of the head base 107.

In yet another embodiment, shown in FIG. 4, shield 130 may be a balloon or other inflatable object 410 that is situated on, in, or otherwise coupled to the head assembly 105, or the head base 107 in a suitable position. The balloon 410 may be inflated to a first inflated position and deflated to a second deflated position, or any position in between, using actuator 118, or other suitable mechanism on the actuator handle assembly 115. In one embodiment, the balloon 410 may initially be provided in an inflated state, and actuator 118 may be used to appropriately deflate balloon 410, for example when the stapler 100 is appropriately positioned in the anus/colon/rectum of a patient. In another embodiment, actuator 118 may be used to both expand and deflate balloon 410. In an inflated position, the balloon 410 may generally partially or fully cover or shield the stapling assembly 230 or head assembly 105 of the stapler, making the stapler 100 easier to pass through an intestinal tract. In a deflated position, the balloon 410 may be retracted into, or alongside the stapling head 107, and trocar 220 can be generally exposed and may be extended.

Figure 13:
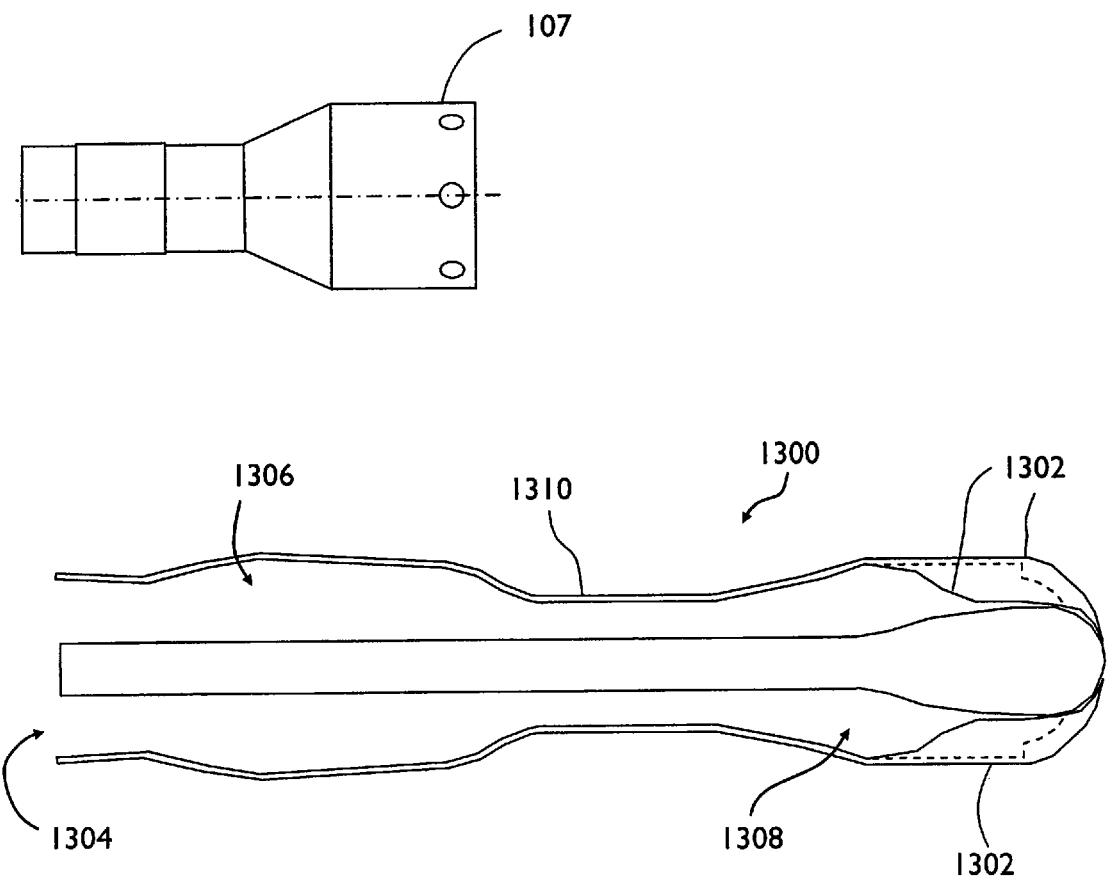
FIG. 13 is a side view of a stapling head and an add-on shield, according to one embodiment of the present disclosure.

In still another embodiment, as mentioned above, the shield may be removably attachable, and may be provided after-market from the surgical stapler itself, such that the shield may be attached to the surgical stapler any time prior to insertion of the stapler through the anus/rectum/colon. An example of an add-on embodiment is illustrated in FIG. 13, which separately shows a surgical stapling head 107 with trocar retracted and an add-on shield 1300. The shield 1300 may include a plurality of shield members 1302, that may generally come together to form a substantially dome-shaped cover for the stapling head 107 once attached to the surgical stapler. While illustrated as substantially dome-shaped, it is recognized that any suitable configuration may be used that generally covers or partially covers the stapling head 107 or stapling head edge(s) and ease passage of the surgical stapler through the anus/colon/rectum of a patient. In the example illustrated, the shield 1300 includes four shield members 1302; however, any other suitable number of shield members 1302 may be used. As with previously described embodiments, the shield members 1302 can be made of any suitable material, including but not limited to, plastic, metal or metal alloy, any other suitable surgical or biocompatible material, or any combination thereof. The shield members 1302 can be flexible, such that upon retraction of the shield 1300 over stapling head 107, as will be described in further detail below, the shield members may flex to an open position, generally uncovering the stapling head 107. In the closed position, in some embodiments, the shield members 1302 may be attached to one another using, for example but not limited to, sutures, peel lines, stress lines, tear lines, perforated lines, or other weakened areas, etc. The shield 1300 includes an opening 1304 at one end for insertion over stapling head 107. The opening 1304 may be flexible such that the shield 1300 may be attached over stapling head 107, but when attached retains a firm grip around the stapling head. The shield 1300 may include a first insertion section 1306 and a second uncovering section 1308. The insertion section 1306 may be generally where the stapling head 107 is held during insertion of the stapling head through the anus/rectum/colon of the patient. As will be described in further detail below, the shield 1300 may be retracted alongside the surgical stapler to bring the stapling head 107 into the uncovering section 1308, where the shield members 1302 may be opened to expose the stapling head 107. Between the insertion section 1306 and the uncovering section 1308, the shield 1300 may have a narrower neck portion 1310 that can help secure the stapling head 107 in either the insertion section 1306 or the uncovering section 1308. In some embodiments, a force may be required to pass the stapling head 107 through the narrower neck portion 1310. The shield 1300 may be provided with a cable or wire, or other actuating means for retracting the shield, in order to pass the stapling head 107 through neck portion 1310.

Figure 14:
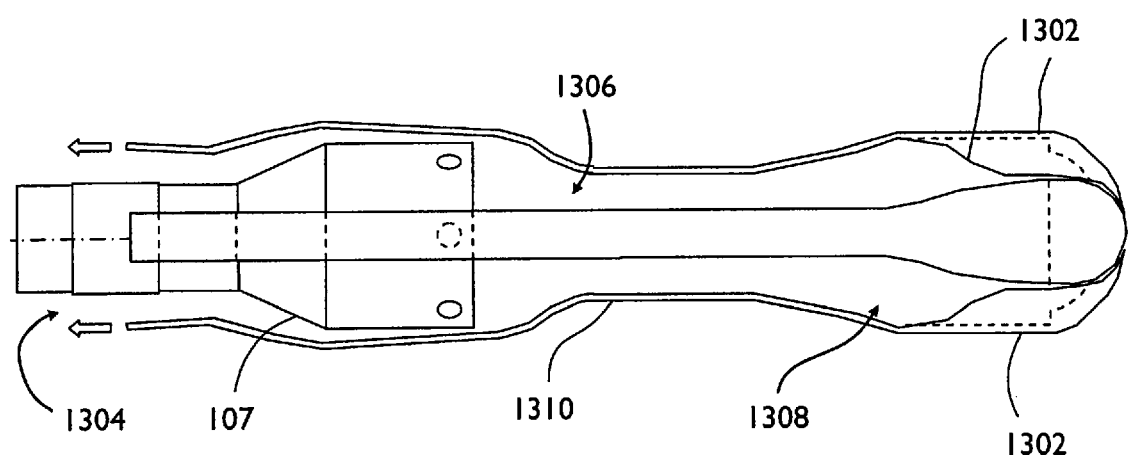
FIG. 14 is a side view of the shield of FIG. 13 attached to the stapling head, according to one embodiment of the present disclosure.

As shown in FIG. 14, the shield 1300 may be generally slid over the stapling head 107 through opening 1304. The stapling head 107 may be positioned within insertion section 1306, which may be sized to generally envelope or partially envelope the stapling head 107. In this position, shown in FIG. 14, the stapling head 107 and shield 1300 may be inserted through the anus/rectum/colon of the patient, with the shield members 1302 providing easier passage of the stapling head 107 through the anus/rectum/colon.

In yet another embodiment, shown in FIGS. 11a-d, a surgical stapler 1000 may include an air or gas pump assembly 1110 that can be used to insufflate the rectum and intestinal tract during insertion and advancement of the stapler 1000. A pump assembly 1110 may include a connector 1120, an external tubing 1130, an internal tubing 1140, and one or more air or gas outlets 1150 in fluid communication with the internal tubing 1140. In such an embodiment, internal tubing 1140 may extend through the interior length of support shaft 122 and optionally through a portion or all of the interior length of handle assembly 115. Connector 1120, as shown in FIGS. 11*a* and 11*b*, may be situated on or adjacent the exterior of handle assembly 115. However, in other embodiments, connector 1120 may be integrated within the handle assembly 115 or positioned at any other suitable location. Connector 1120 may operably and removably couple internal tubing 1140 and external tubing 1130. As shown in FIG. 11*c*, external tubing 11*c* may include a bladder or reservoir 1132 and/or a bulb 1134 with a one way valve 1136, which can be manually pumped to force air or gas through external tubing 1130, into internal tubing 1140, and out air or gas outlets 1150. In other embodiments, the external tubing may be mechanically pumped, or pumped using a combination of mechanical and manual methods for forcing air or gas into the internal tubing 1140. Internal tubing 1140 and external tubing 1130 can be made of any suitable material such as rubber, plastic, any other suitable material, or any combination of suitable materials. Internal tubing 1140 may extend from connector 1120 to head base 107. Stapling assembly 230 may include one or more air or gas outlets 1150 to allow the escape of air or gas from the internal tubing 1140 to insufflate the rectum and intestinal tract. In one embodiment, for example, the air or gas outlets 1150 may be positioned between trocar 220 and cutting blade 250. However, the outlets 1150 may be positioned at any other location suitable for insufflation of the rectum and intestinal tract. When bulb 1134 and/or bladder 1132 of external tubing 1130 are pumped, air or gas can be forced from external tubing 1130 to internal tubing 1140, and finally through air outlet 1150. The force of the air or gas pumped through the air pump assembly can insufflate the intestinal or rectal cavity into which the stapler has been passed. In this way, strictures and other naturally occurring obstacles in an intestinal wall may be dilated such that the stapler may be more easily navigated through the intestine. This may significantly decrease the amount of trauma caused to the intestine. The embodiment shown in FIGS. 11*a-d* could be used with or without a retractable shield as described herein. The pump assembly could also be used with or without an anvil attached to the head assembly.

Figure 6:
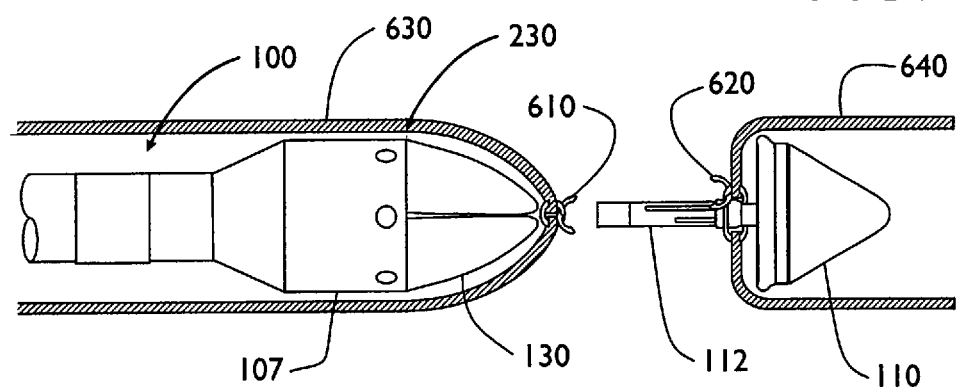
FIG. 6 is a perspective view illustrating a double purse string suture method of constructing an anastomosis with a surgical stapler, according to one embodiment of the present disclosure, whereby an anvil portion of a stapler is inserted into a proximal lumen and an anvil-less portion of a stapler is inserted in a distal lumen in accordance with one embodiment of the present disclosure.
Figure 7:
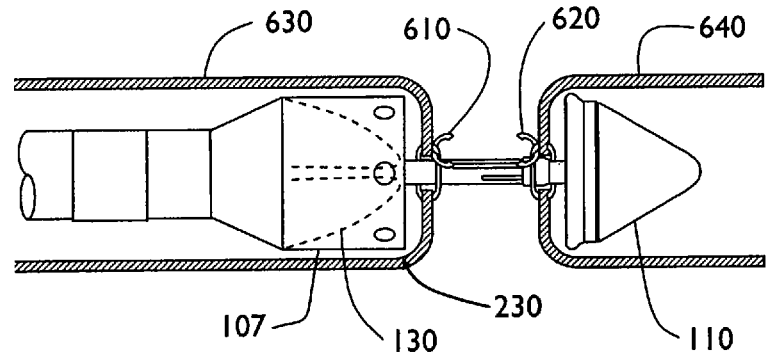
FIG. 7 is a perspective view illustrating the positioning of a stapler and a proximal and distal lumen in relation to the stapler just prior to stapling, wherein the distal lumen has been secured by a purse string suture, in accordance with an embodiment of the present disclosure

Having described various embodiments of a surgical stapler according to the present disclosure, methods of creating an anastomosis using a stapler according to certain embodiments of the present disclosure are now described. FIGS. 5, 6, and 7 show one method 500 of a surgical stapler 100 being used to create an anastomosis by means of a double purse string suture technique. According to step 510, in preparation for the anastomosis, purse string sutures 610, 620 may be placed in both the distal 630 and proximal 640 ends of the lumen to be connected. In step 520, the anvil 110 can be inserted into the proximal intestinal lumen 640, and in step 530, the purse string suture 620 can then be pulled together, gathering the end of the lumen about the anvil shaft 112, thereby exposing the anvil shaft 112. According to step 540, the surgical stapler 100 with the anvil 110 unattached can be inserted through the anus and through the rectal cavity an appropriate length or distance of the distal intestinal tract 630. With previous surgical staplers, because portions of the stapling assembly of such staplers may not be smooth and/or streamlined surfaces, during passage of the stapler without any cover for the stapling assembly risk of trauma or irritation to the bowel is increased. Additionally, previous surgical staplers without a suitable cover for the stapling assembly may not be easily navigated through the bowel because of strictures, valves, curves or twists in the intestinal wall.

Thus, in one embodiment of the present disclosure as shown in FIG. 6, shield 130, which may allow stapling assembly 230 to become more streamlined or navigable, and may further allow for easier navigation of stapling assembly 230 through the intestinal tract 630, can be generally partially or fully extended over the stapling assembly 230. In some embodiments, stapler 100 may be initially provided with shield 130 extended. In other embodiments, shield 130 may be extended using actuator 118, as described above. Shield 130, according to the present disclosure, may significantly reduce the problems that are inherent in the double purse string suture method of creating an anastomosis. When shield 130 is extended over the stapling assembly 230 of stapler 100, the design of stapler 100 can become more streamlined and/or generally smooth, so that stapling assembly 230 of stapler 100 can be more easily navigated through the intestine, thereby reducing or eliminating trauma to the intestine that can be caused by pronounced or sharp surfaces. Additionally, the streamlined design formed by shield 130 of stapler 100 may help navigate by or through strictures, valves, curves or twists in an intestinal wall.

According to step 550, when the stapling assembly 230 of stapler 100 has been appropriately positioned adjacent or near the purse string 610 of the distal lumen 630, shield 130 may be retracted into or alongside the outer circumference of head base 107 using actuator 118 or other suitable mechanism to generally partially or fully expose the stapling assembly 230. In step 560, the trocar 220 may be extended from stapling assembly 230, for example using actuator 116. Purse string suture 610 may be opened wide enough to allow trocar 220 to be passed through. In step 570, trocar 220 and anvil shaft 112 may be joined, as illustrated in FIG. 7. FIG. 7 shows the positioning of stapler 100 according to one embodiment of the present disclosure just prior to engaging the stapling mechanism. In step 580, actuator 117 may be activated to cause the anvil 110 to contact head base 107, thereby causing the proximal and distal lumens to be stapled together, as is known to those skilled in the art. Once the anastomosis is completed, in step 590, the stapler 100, with anvil 110 attached to stapling assembly 230, may be removed from the patient.

In some previous double purse string suture techniques, in order to more easily navigate an intestinal tract of a patient, the anvil is not initially removed from the stapler, but is inserted into the intestinal tract attached to the stapler. In such techniques, the anvil may have created a somewhat streamlined surface for navigating the intestinal tract. However, this technique still retains disadvantages overcome by the various embodiments of the present disclosure. In using the previous technique, once the head assembly is appropriately positioned near the purse string suture at the distal end of the lumen, the purse string suture needed to be opened wide enough to allow the entire anvil to pass through the purse string suture of the distal lumen and into the proximal lumen. Opening the purse string suture of the distal lumen wide enough to allow the anvil to pass through the distal lumen may significantly increase the risks associated with bowel leakage, such as increased rates of postoperative infection. The attendant harm of bowel leakage associated with this technique may negate any advantages associated with leaving the anvil attached to the stapling assembly as it is passed through the patient's intestinal tract.

In contrast, as described above, using shield 130 of the present disclosure allows stapling assembly 230 to be easily navigated through the intestinal tract 630 with the anvil 110 unattached from the stapling assembly 230. When the stapling assembly 230 is appropriately positioned, shield 130 may be retracted generally partially or fully exposing trocar 220. Using this technique of the present disclosure, the purse string 610 does not need to be opened so wide as to allow an entire anvil 110 through, but instead, the amount purse string 610 needs to be opened can be minimized to the diameter or substantially the diameter of the trocar 220, which is generally substantially smaller than the diameter of anvil 110, thereby reducing the risks associated with bowel leakage.

If it is determined, in some cases, that an increased risk of bowel leakage associated with this technique does not outweigh the advantage of inserting the stapler with the anvil attached, the present disclosure still retains advantages over previous techniques. The various embodiments of the present disclosure allow for the shield to cover the head assembly, which includes the anvil. Thus, in instances where the anvil may have surfaces that are not smooth, or that otherwise make it relatively more difficult to navigate an intestinal tract, a shield according to the present disclosure may extend over the head assembly including the anvil, making it easier to navigate the intestinal tract of a patient.

Figure 8:
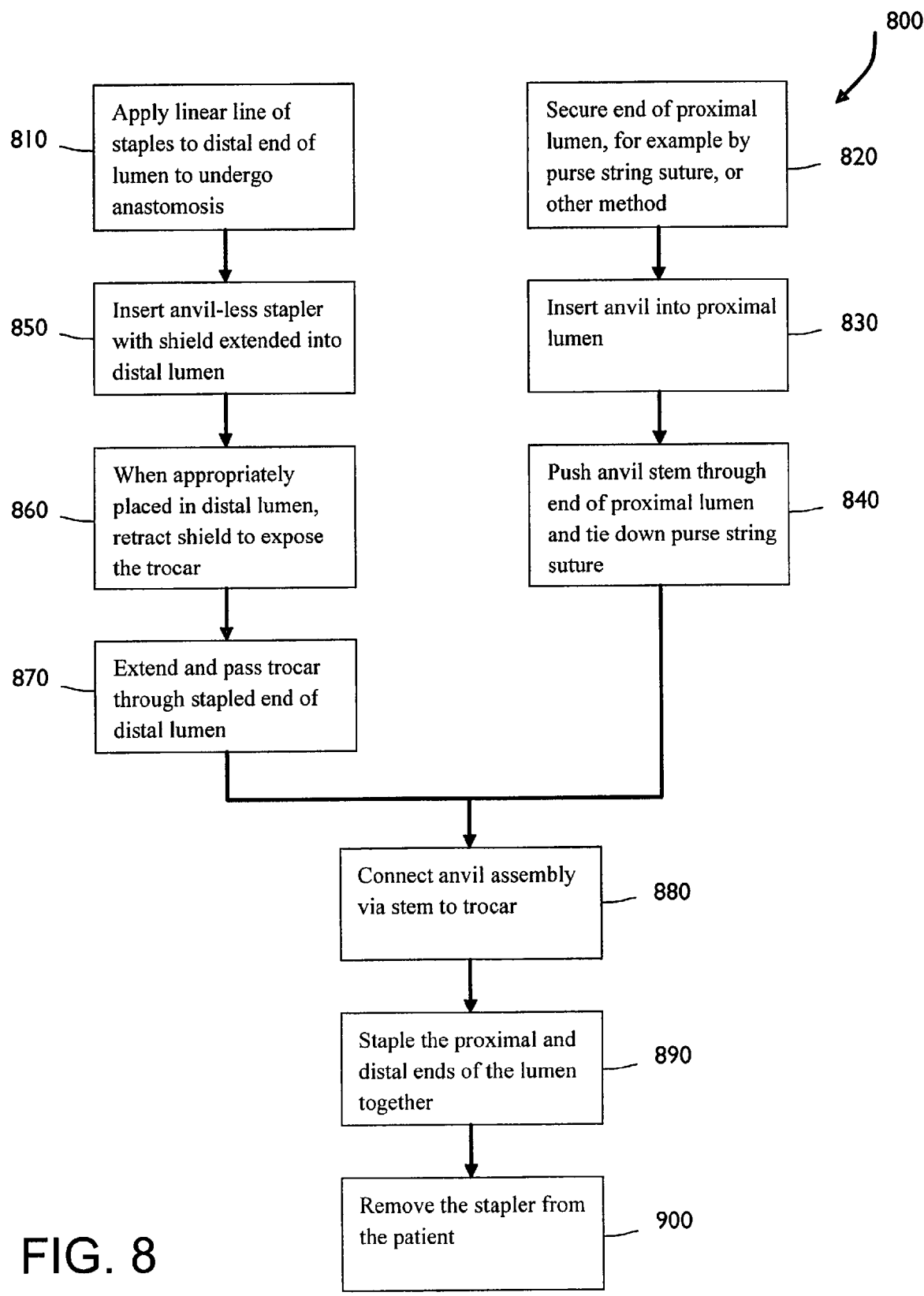
FIG. 8 is a flow diagram of a method for constructing an anastomosis with a surgical stapler with a retractable shield or cover, according to one embodiment of the present disclosure, by using staples to secure the end of a distal lumen, and another securing mechanism to secure the end of the proximal lumen.
Figure 9:
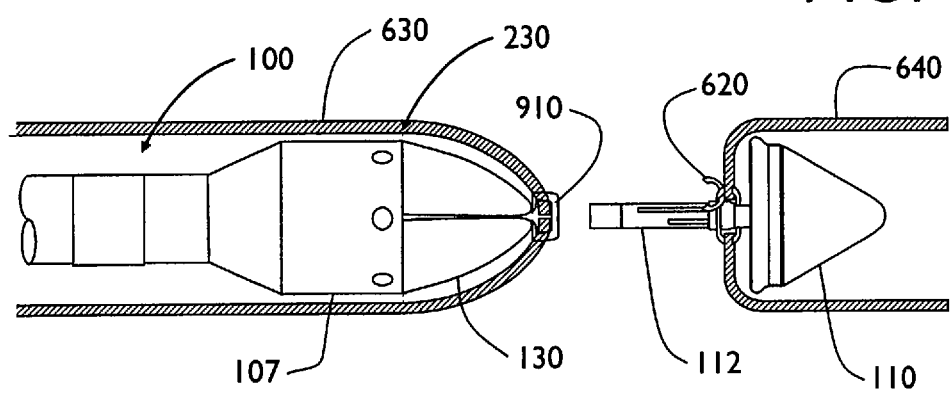
FIG. 9 is a perspective view illustrating a method of constructing an anastomosis with a surgical stapler wherein the distal lumen is secured by staples, according to one embodiment of the present disclosure, whereby an anvil portion of a stapler is inserted into a proximal lumen and an anvil-less portion of a stapler is inserted in a distal lumen in accordance with one embodiment of the present disclosure.
Figure 10:
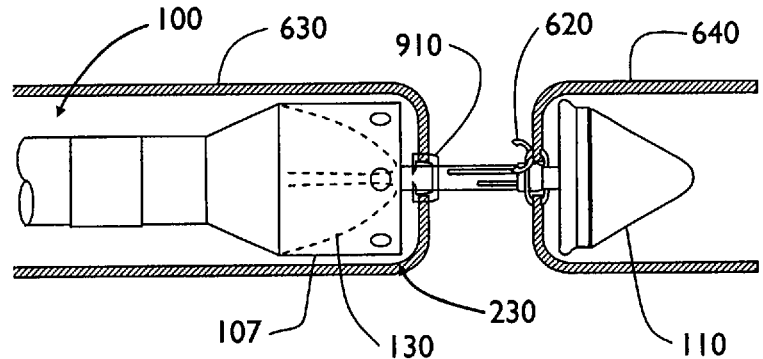
FIG. 10 is a perspective view illustrating the positioning of a stapler and a proximal and distal lumen in relation to the stapler just prior to stapling, wherein the distal lumen has been secured by staples, in accordance with an embodiment of the present disclosure.

Another method 800 for creating an anastomosis according to the present disclosure is illustrated in FIGS. 8, 9 and 10. This technique is commonly known as the double staple technique. In step 810, a linear line of staples 910 may be applied to close the end of the distal lumen 630, as shown in FIG. 9. In step 820, staples, a purse string suture, or other suitable means may be used to close the end of the proximal lumen 640. In some embodiments, this method can be advantageous over the previously discussed method because it does not use a purse string suture about the end of the distal lumen, which can be difficult to apply and may increase the risk of bowel leakage. Otherwise, the method 800 may be performed in generally a similar manner as the double purse string method 500 described above.

Particularly, in step 830, the anvil 110 can be inserted into the proximal intestinal lumen 640, and in step 840, in one embodiment the purse string suture 620 can then be pulled together, gathering the end of the lumen about the anvil shaft 112, thereby exposing the anvil shaft 112. According to step 850, the surgical stapler 100 with the anvil 110 unattached can be inserted through the anus and through the rectal cavity an appropriate length or distance of the distal intestinal tract 630. With previous surgical staplers, as stated above, portions of the stapling assembly of such staplers may not be smooth and/or streamlined surfaces. Therefore, during passage of the stapler without an anvil portion attached or without any other cover for the stapling assembly, risk of trauma or irritation to the bowel is increased. Additionally, previous surgical staplers without an anvil attached or other suitable cover for the stapling assembly may not be easily navigated through the bowel because of strictures, and naturally occurring valves and curves in the intestinal wall.

Thus, in one embodiment of the present disclosure as shown in FIG. 9, shield 130, which may allow the stapling assembly 230 to become more streamlined or navigable, and may further allow for easier navigation of the stapling assembly 230 through the intestinal tract 630, can be generally partially or fully extended over the stapling assembly 230. In some embodiments, stapler 100 may be initially provided with shield 130 extended. In other embodiments, shield 130 may be extended using actuator 118, as described above. Shield 130, according to the present disclosure, may significantly reduce the problems that are inherent in prior methods of creating an anastomosis. When shield 130 is extended over the stapling assembly 230 of stapler 100, the design of the stapler 100 can become more streamlined and or generally smooth, so that the stapling assembly 230 of stapler 100 can be more easily navigated through the intestine, thereby reducing or eliminating trauma to the intestine that can be caused by pronounced or sharp surfaces. Additionally, the streamlined design formed by shield 130 of stapler 100 may help navigate by or through strictures and naturally occurring valves and curves in an intestinal wall.

According to step 860, when the stapling assembly 230 of stapler 100 has been appropriately positioned adjacent or near the linear staple line 910 of the distal lumen 630, shield 130 may be retracted into, or alongside the outer circumference of head base 107 using actuator 118 or other suitable mechanism to generally partially or fully expose stapling assembly 230. In step 870, the trocar 220 may be extended from stapling assembly 230, for example using actuator 116. Trocar 220 may then be pushed, forced, or otherwise passed through the stapled end of the distal lumen 630. In step 880, trocar 220 and anvil shaft 112 may be joined, as illustrated in FIG. 10. FIG. 10 shows the positioning of stapler 100 according to one embodiment of the present disclosure just prior to engaging the stapling mechanism. In step 890, actuator 117 may be activated to cause the anvil 110 to contact head base 107, thereby causing the proximal and distal lumens to be stapled together, as is known to those skilled in the art. Once the anastomosis is completed, in step 900, the stapler 100, with anvil 110 attached to stapling assembly 230, may be removed from the patient.

Figure 15:
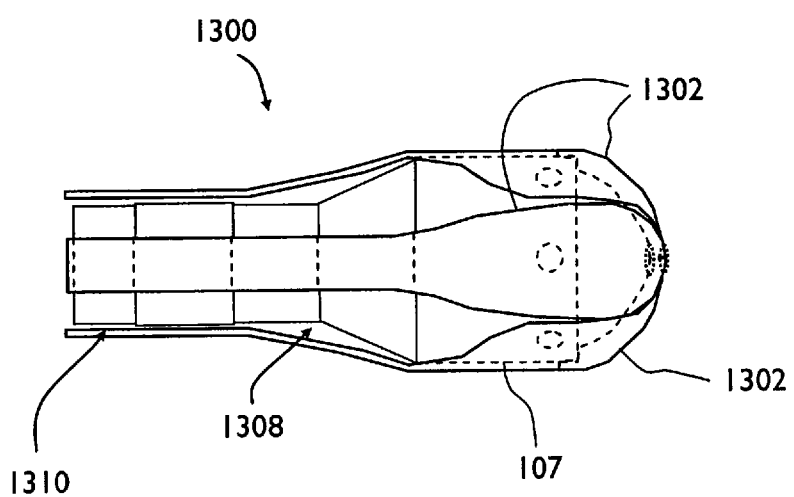
FIG. 15 is a side view of the shield of FIG. 13 retracted such that the stapling head is in the uncovering section of the shield, according to one embodiment of the present disclosure.
Figure 16A:
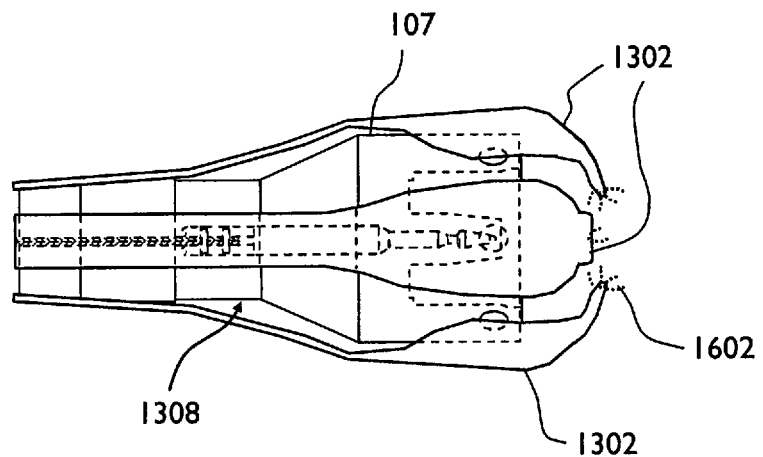
FIG. 16a is a side view of the stapling head and shield of FIG. 15 wherein the shield members have begun separating, according to one embodiment of the present disclosure.
Figure 16B:
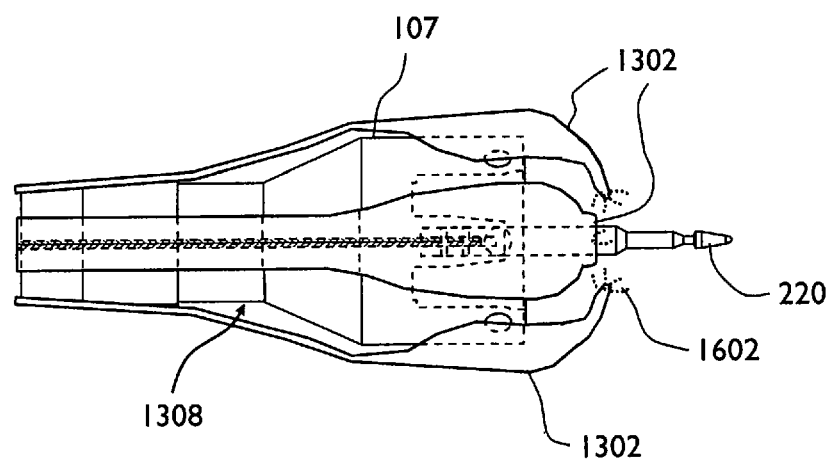
FIG. 16b is a side view of the stapling head and shield of FIG. 15 wherein the trocar has been used to separate the shield members, according to one embodiment of the present disclosure.
Figure 17:
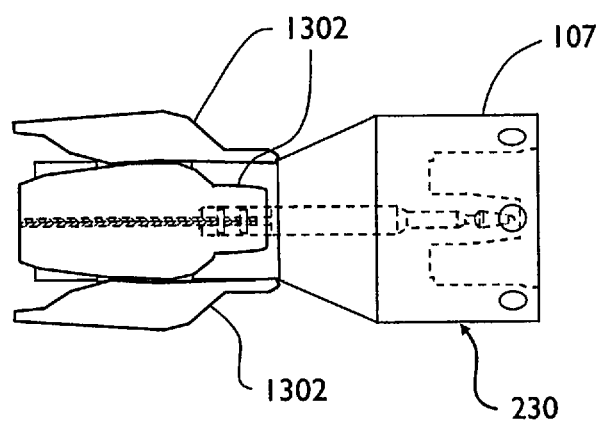
FIG. 17 is a side view of the stapling head and shield of FIG. 15 wherein the shield members have been generally fully retracted to expose the stapling head, according to one embodiment of the present disclosure.

A method of creating an anastomosis using a stapler and add-on shield according to certain embodiments of the present disclosure, such as that illustrated in FIGS. 13 and 14 may be carried out in generally the same manner as described above with integral stapler/shield embodiments. However, prior to insertion of the stapler through the anus and through the rectal cavity, the add-on shield 1300 may be attached to the stapling head 107, as described above and shown in FIG. 14, with the stapling head 107 held generally within the insertion section 1306. When the uncovering section 1308 of shield 1300, and therefore the distal end of shield members 1302, has been appropriately positioned adjacent or near the purse string of the distal lumen, shield 1300 may be retracted alongside the outer circumference of head base 107. The shield may be provided with a cable or wire, or other suitable actuating means for retracting the shield 1300. Upon retraction of the shield 1300, the stapling head 107 may be forced from the insertion section 1306, through the neck portion 1310, and into uncovering section 1308, as shown in FIG. 15. In one embodiment, moving the stapling head 107 into uncovering section 1308 may cause shield members 1302 to separate, and in some embodiments, break the sutures 1602 holding the shield members 1302 together, as illustrated in FIG. 16*a*. However, in other embodiments, the shield members, and sutures 1602 if used, may be separated in a separate step, or in some cases by further retracting shield 1300. In alternative embodiments, as shown in FIG. 16*b*, the trocar 220 may be used to pierce the shield members 1302 and/or sutures 1602 to separate the shield members. In any case, separated shield members 1302 may be retracted back alongside the surgical stapler, as shown for example in FIG. 17, to generally partially or fully expose the stapling assembly. The remainder of the anastomosis may be carried out as described above.

Although the present invention has been described with reference to preferred embodiments, persons skilled in the art will recognize that changes may be made in form and detail without departing from the spirit and scope of the present disclosure. For example, it is appreciated that other suitable mechanisms may be used to create a cover or shield for stapling assembly 230 or head assembly 105 and are within the spirit and scope of the present disclosure.

We claim:

1. A surgical stapler comprising:
   a stapling assembly having a trocar;
   an anvil having an anvil shaft removably detachable with the trocar; and
   a retractable shield comprising a base portion having a first end defining an opening and a plurality of shield segments, each segment having a single piece construction and having an arc-shape with a continuous or solid outer circumferential surface and a tip end and a base end, the segments configured to slidably extend from the base portion in a first extended position where the tips of the shield segments form a generally dome-shaped tip at least partially covering the stapling assembly, and slidably retract to a second retracted position at least partially retracted into the base portion where the shield segments generally expose the stapling assembly.

2. The surgical stapler of claim 1, wherein the base portion of the shield is integral with the stapling assembly.

3. The surgical stapler of claim 1, wherein the shield segments are a plurality of petal-like members.

4. The surgical stapler of claim 3, wherein the shield segments comprise one or more weakened areas wherein adjacent shield segments are adjoined and at which the shield segments separate when actuated to the second retracted position.

5. The surgical stapler of claim 1, wherein the shield is removably attachable to the stapling assembly.

6. The surgical stapler of claim 1, further comprising an actuator for controlling extending and retracting of the shield.

7. The surgical stapler of claim 1, further comprising a flexible shaft assembly.

8. The surgical stapler of claim 1, wherein:
   in the extended position, the tip end of each shield segment is distal to the first end of the base portion, and
   in a fully retracted position, the tip end of each shield segment is proximal to the first end of the base portion.

* * * * *